(12) United States Patent
Kariathungal et al.

(10) Patent No.: US 8,036,917 B2
(45) Date of Patent: Oct. 11, 2011

(54) METHODS AND SYSTEMS FOR CREATION OF HANGING PROTOCOLS USING EYE TRACKING AND VOICE COMMAND AND CONTROL

(75) Inventors: Murali Kumaran Kariathungal, Hoffman Estates, IL (US); Prakash Mahesh, Hoffman Estates, IL (US); Mark Morita, Arlington Heights, IL (US); Stephen P. Roehm, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 853 days.

(21) Appl. No.: 11/749,625

(22) Filed: May 16, 2007

(65) Prior Publication Data

US 2008/0120141 A1 May 22, 2008

Related U.S. Application Data

(60) Provisional application No. 60/867,064, filed on Nov. 22, 2006.

(51) Int. Cl.
*G06Q 50/00* (2006.01)
(52) U.S. Cl. .............................. 705/3; 715/700; 600/300
(58) Field of Classification Search .................. 705/2–3; 715/700; 600/300
See application file for complete search history.

(56) References Cited

U.S. PATENT DOCUMENTS

| 5,635,947 | A | * | 6/1997 | Iwamoto | 345/7 |
| 5,802,220 | A | * | 9/1998 | Black et al. | 382/276 |
| 6,243,076 | B1 | * | 6/2001 | Hatfield | 345/156 |
| 6,421,064 | B1 | * | 7/2002 | Lemelson et al. | 345/688 |
| 6,795,806 | B1 | * | 9/2004 | Lewis et al. | 704/260 |
| 7,050,078 | B2 | * | 5/2006 | Dempski | 715/700 |
| 2002/0120424 | A1 | * | 8/2002 | Hauger et al. | 702/150 |
| 2004/0113888 | A1 | * | 6/2004 | De Waal | 345/157 |
| 2006/0208169 | A1 | * | 9/2006 | Breed et al. | 250/221 |
| 2006/0277073 | A1 | * | 12/2006 | Heilbrunn et al. | 705/3 |
| 2007/0011609 | A1 | * | 1/2007 | Adjouadi et al. | 715/700 |

* cited by examiner

*Primary Examiner* — Gerald J. O'Connor
*Assistant Examiner* — Sind Phongsvirajati
(74) *Attorney, Agent, or Firm* — Hanley, Flight & Zimmerman, LLC

(57) ABSTRACT

Certain embodiments of the present invention provide methods and systems for hanging protocol generation using eye tracking and/or voice command and control. Certain embodiments provide a method for creating a hanging protocol based on at least one of eye tracking and voice command and control input in a clinical environment. The method includes specifying a hanging protocol specification using input including at least one of eye tracking and voice command and control. The method also includes translating the input into a hanging protocol. The method further includes facilitating display of clinical information based on the hanging protocol.

9 Claims, 6 Drawing Sheets

METHODS AND SYSTEMS FOR CREATION OF HANGING PROTOCOLS USING EYE TRACKING AND VOICE COMMAND AND CONTROL

RELATED APPLICATIONS

This application claims priority to a provisional application entitled "Methods and Systems for Creation of Hanging Protocols Using Eye Tracking and Voice Command and Control," filed on Nov. 22, 2006, as Ser. No. 60/867,064, which is herein incorporated by reference in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to improving healthcare application workflow. In particular, the present invention relates to use of eye tracking and voice command and control to improve healthcare application workflow through creation of hanging protocols.

A clinical or healthcare environment is a crowded, demanding environment that would benefit from organization and improved ease of use of imaging systems, data storage systems, and other equipment used in the healthcare environment. A healthcare environment, such as a hospital or clinic, encompasses a large array of professionals, patients, and equipment. Personnel in a healthcare facility must manage a plurality of patients, systems, and tasks to provide quality service to patients. Healthcare personnel may encounter many difficulties or obstacles in their workflow.

In a healthcare or clinical environment, such as a hospital, a large number of employees and patients may result in confusion or delay when trying to reach other medical personnel for examination, treatment, consultation, or referral, for example. A delay in contacting other medical personnel may result in further injury or death to a patient. Additionally, a variety of distraction in a clinical environment may frequently interrupt medical personnel or interfere with their job performance. Furthermore, workspaces, such as a radiology workspace, may become cluttered with a variety of monitors, data input devices, data storage devices, and communication device, for example. Cluttered workspaces may result in efficient workflow and service to clients, which may impact a patient's health and safety or result in liability for a healthcare facility.

Data entry and access is also complicated in a typical healthcare facility. Speech transcription or dictation is typically accomplished by typing on a keyboard, dialing a transcription service, using a microphone, using a Dictaphone, or using digital speech recognition software at a personal computer. Such dictation methods involve a healthcare practitioner sitting in front of a computer or using a telephone, which may be impractical during operational situations. Similarly, for access to electronic mail or voice messages, a practitioner must typically use a computer or telephone in the facility. Access outside of the facility or away from a computer or telephone is limited.

Thus, management of multiple and disparate devices, positioned within an already crowded environment, that are used to perform daily tasks is difficult for medical or healthcare personnel. Additionally, a lack of interoperability between the devices increases delay and inconvenience associated with the use of multiple devices in a healthcare workflow. The use of multiple devices may also involve managing multiple logons within the same environment. A system and method for improving ease of use and interoperability between multiple devices in a healthcare environment would be highly desirable.

In a healthcare environment involving extensive interaction with a plurality of devices, such as keyboards, computer mousing devices, imaging probes, and surgical equipment, repetitive motion disorders often occur. A system and method that eliminates some of the repetitive motion in order to minimize repetitive motion injuries would be highly desirable.

Healthcare environments, such as hospitals or clinics, include clinical information systems, such as hospital information systems (HIS) and radiology information systems (RIS), and storage systems, such as picture archiving and communication systems (PACS). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during surgery, medical personnel may access patient information, such as images of a patient's anatomy, that are stored in a medical information system. Alternatively, medical personnel may enter new information, such as history, diagnostic, or treatment information, into a medical information system during an ongoing medical procedure.

In current information systems, such as PACS, information is entered or retrieved using a local computer terminal with a keyboard and/or mouse. During a medical procedure or at other times in a medical workflow, physical use of a keyboard, mouse or similar device may be impractical (e.g., in a different room) and/or unsanitary (i.e., a violation of the integrity of an individual's sterile field). Re-sterilizing after using a local computer terminal is often impractical for medical personnel in an operating room, for example, and may discourage medical personnel from accessing medical information systems. Thus, a system and method providing access to a medical information system without physical contact would be highly desirable to improve workflow and maintain a sterile field.

Imaging systems are complicated to configure and to operate. Often, healthcare personnel may be trying to obtain an image of a patient, reference or update patient records or diagnosis, and ordering additional tests or consultation. Thus, there is a need for a system and method that facilitate operation and interoperability of an imaging system and related devices by an operator.

In many situations, an operator of an imaging system may experience difficulty when scanning a patient or other object using an imaging system console. For example, using an imaging system, such as an ultrasound imaging system, for upper and lower extremity exams, compression exams, carotid exams, neo-natal head exams, and portable exams may be difficult with a typical system control console. An operator may not be able to physically reach both the console and a location to be scanned. Additionally, an operator may not be able to adjust a patient being scanned and operate the system at the console simultaneously. An operator may be unable to reach a telephone or a computer terminal to access information or order tests or consultation. Providing an additional operator or assistant to assist with examination may increase cost of the examination and may produce errors or unusable data due to miscommunication between the operator and the assistant. Thus, a method and system that facilitates operation of an imaging system and related services by an individual operator would be highly desirable.

Additionally, image volume for acquisition and radiologist review continues to increase. PACS imaging tools have increased in complexity as well. Thus, interactions with standard input devices (e.g., mouse, trackball, etc.) have become increasingly more difficult. Radiologists have complained about a lack of ergonomics with respect to standard input devices, such as a mouse, trackball, etc. Scrolling through large datasets by manually cine-ing or scrolling, repeated mouse movements, and other current techniques have resulted in carpel tunnel syndrome and other repetitive stress syndromes. Radiologists have not been able to leverage other, more ergonomic input devices (e.g., joysticks, video editors, game pads, etc.), because the devices are not custom configurable for PACS and other healthcare application interactions.

A hanging protocol is a set of display rules for presenting, formatting and otherwise organizing images on a display device of a PACS workstation, for example. A display rule is a convention for presenting one or more images in a particular temporal and/or spatial layout or sequence. For example, a hanging protocol may include a set of computer-readable instructions (or display rules, for example) that direct a computer to display a plurality of images in certain locations on a display device and/or display the plurality of images in a certain sequence or order. In another example, a hanging protocol may include a set of computer-readable instructions that direct a computer to place a plurality of images in multiple screens and/or viewports on a display device. In general, a hanging protocol may be employed to present a plurality of images for a diagnostic examination of a patient anatomy featured in the images.

A hanging protocol may direct, for example, a PACS workstation to display an anterior-posterior ("AP") image adjacent to a lateral image of the same anatomy. In another example, a hanging protocol may direct PACS workstation to display the AP image before displaying the lateral image. In general, a hanging protocol dictates the spatial and/or temporal presentation of a plurality of images at PACS workstation.

A hanging protocol differs from a default display protocol ("DDP"). In general, a DDP is a default workflow that applies a series of image processing functions to image data. The image processing functions are applied to the image data in order to present an image (based on the image data) to a user. The image processing functions alter the appearance of image data. For example, an image processing function may alter the contrast level of an image.

DDPs typically include processing steps or functions that are applied before any diagnostic examination of the images. For example, processing functions may be applied to image data in order to enhance features within an image (based on the image data). Such processing functions can include any software-based application that may alter a visual appearance or representation of image data. For example, a processing function can include any one or more of flipping an image, zooming in an image, panning across an image, altering a window and/or level setting in a representation of the image data, and altering a contrast and/or brightness setting in a representation of the image data.

DDPs are usually based on a type of imaging modality used to obtain the image data. For example, image data obtained with a C-arm imaging device in general or a particular C-arm imaging device may have a same or similar DDP applied to the image data. In general, a DDP attempts to present image data in a manner most useful to many users. Conversely, applying a hanging protocol to image data does not alter the appearance of an image (based on the image data), but instead dictates how the image(s) is(are) presented, as described above.

Hanging protocols are currently created using one or more of a mouse, keyboard and graphical user interface ("GUI") components. Such components are used to specify an image box type (for example, stack, sheet, volume, etc.). The components are used to specify parameters for image sets to be loaded in the image box. The components are also used to set image view presets and/or presentation state, for example. Current hanging protocol creation involves multiple input devices, and a user must switch between keyboard and mouse to create a hanging protocol.

Thus, there is a need for systems and methods to improve healthcare workflow using eye tracking and voice command and control and other interaction. Systems and methods for improved creation and management of hanging protocols would also be highly desirable.

BRIEF SUMMARY OF THE INVENTION

Certain embodiments of the present invention provide methods and systems for hanging protocol generation using eye tracking and/or voice command and control.

Certain embodiments provide a method for creating a hanging protocol based on at least one of eye tracking and voice command and control input in a clinical environment. The method includes specifying a hanging protocol specification using input including at least one of eye tracking and voice command and control. The method also includes translating the input into a hanging protocol. The method further includes facilitating display of clinical information based on the hanging protocol.

Certain embodiments provide a method for hanging protocol creation and management using eye tracking and voice command and control input in a clinical environment. The method includes initiating hanging protocol creation using at least one of eye tracking and voice command input. The method also includes specifying a body part for the hanging protocol using at least one of eye tracking and voice command input. The method further includes specifying a clinical procedure for the hanging protocol using at least one of eye tracking and voice command input. Additionally, the method includes identifying a number of monitors for use in the hanging protocol using at least one of eye tracking and voice command input. The method includes defining at least one of a monitor color and monitor resolution for one or more monitors in the hanging protocol using at least one of eye tracking and voice command input. The method also includes specifying a number and type of image box for a viewing region in the one or more monitors in the hanging protocol using at least one of eye tracking and voice command input. In addition, the method includes specifying a number of images to be tiled in an image box in the hanging protocol using at least one of eye tracking and voice command input.

Certain embodiments provide a computer-readable medium having a set of instructions for execution on a computer. The set of instructions includes an input routine receiving user input to configure a hanging protocol for clinical information viewing. The user input includes eye tracking and voice command and control. The set of instructions also includes a hanging protocol configuration routine translating the user input into a hanging protocol for facilitating display of clinical information.

Figure 1:
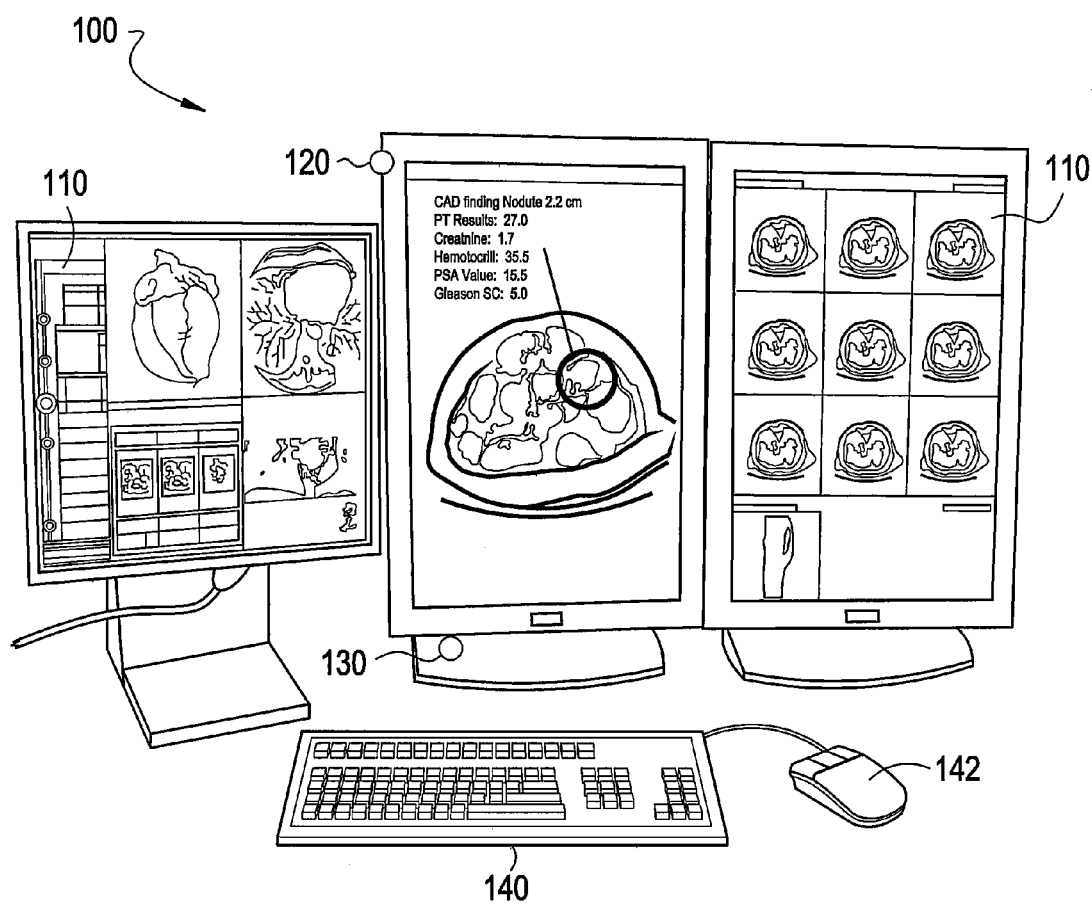
FIG. 1 illustrates an improved display system for selecting and displaying information in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates an improved display system 100 for selecting and displaying information in accordance with an embodiment of the present invention. The system 100 includes a display 110, a tracking device 120, microphone 130, and manual input devices 140, 142. The components of the system 100 may communicate via wired, wireless and/or infrared communication, for example. The components of the system 100 may be implemented separately and/or integrated in various forms, for example.

As shown in FIG. 1, one or more simple display devices 110 may be used to display information to a user. The display 110 may be used with a camera and/or a portable eyewear and eye tracking system, such as a gaze or visual tracking system including the tracking device 120, to display information for one or more users. By tracking where a user is focusing or fixating his or her visual attention, an accurate measure of user intent may be inferred. Eye or gaze tracking may be faster and more efficient than a mechanical pointing or selecting device, such as a keyboard 140 or mouse 142.

Additionally, voice commands and/or gesture control using cameras, such as fire-wire web cams, may allow interaction with imaging and information systems without disrupting a sterile field. The tracking device 120 may be used in conjunction with gesture control, for example. The microphone 130 may be used in conjunction with voice or subvocal command and control, for example.

The tracking device 120 may be a camera, for example. The tracking device 120 may work instead of and/or in conjunction with a headset or eyewear worn by a user, for example (not shown). The tracking device 120 may be attached to the display device 110, such as on a side or top of the display device 110.

A visual or gaze tracking system may be based on a camera system (e.g., visible light or infrared), for example, and may be active or passive. Alternatively or in addition, a user's gaze may be tracked based on movement of the user's head via a camera or position sensor, for example. Multiple cameras may be used to track a location of a user's gaze. Additionally, multiple cameras may be used to drive a cursor or other indicator on a display, such as the display device 110. The gaze tracking system may include head gear, such as goggles or other ocular device, for a user to wear and/or may use a display-mounted camera or sensor, for example. In an embodiment, the gaze tracking system is calibrated for a user. By tracking a user's gaze, a system may initiate communication, selection, and/or function at a remote system, for example.

Figure 2:
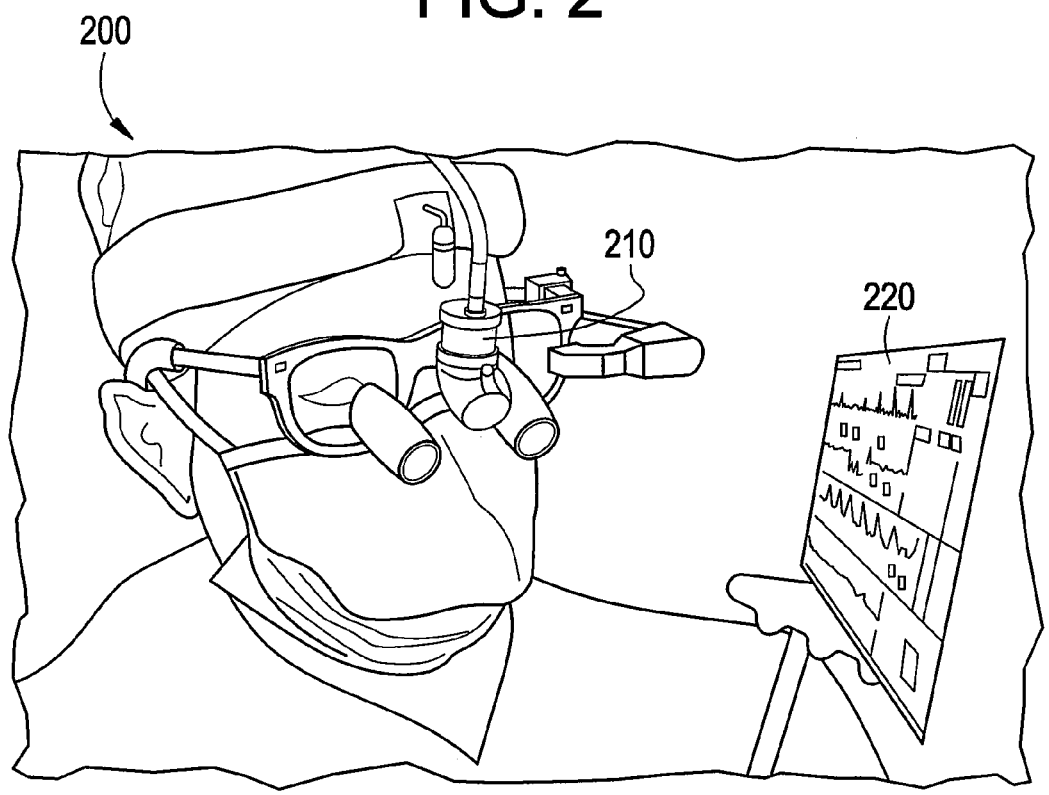
FIG. 2 illustrates a portable eyewear viewing system used in accordance with an embodiment of the present invention.

FIG. 2 depicts a portable eyewear viewing system 200 used in accordance with an embodiment of the present invention. The system 200 includes an eyewear headset 210, a personal eyewear display 220, and a gaze tracking processor 230. The processor 230 may be integrated into the eyewear 210 and/or separate from the eyewear 210. The personal eyewear display 220 is projected in a user's field of view by the eyewear 210.

A healthcare practitioner may use eyewear 210, such as goggles, to capture the practitioner's gaze and perform interface navigation. A user's gaze may be tracked via infrared or other light source, for example. Light may be reflected off of the user's pupil(s) and detected. Light may also be reflected off of the front and rear surfaces of the cornea(s) and lenses of the user's eye(s) and detected or recorded. Repeated measurements track a change in the user's gaze. Alternatively or in addition, a user's gaze may be tracked based on movement of the user's head via a camera or position sensor, for example. A position of the user's gaze and/or head in a reference coordinate system and/or with respect to a reference point, such as a location on a display, may be determined. In an embodiment, a plurality of measurements may be obtained to determine a user's line of sight and/or head angle, for example.

In an embodiment, goggles or other eyewear may also project images into a user's oculars or provide a miniature screen attached to the eyewear 210 and positioned in the user's field of vision to form a virtual personal display 220. Thus, eyewear 210 may be used to eliminate some displays in the healthcare environment. Additionally, eyewear 210 may allow specific information to be targeted for display for specific users in the healthcare environment. For example, a nurse, an anesthesiologist, and a surgeon receive different information displayed on their personal eyewear display 220. For example, a surgeon may view image-guided surgery and PACS data while an anesthesiologist views EKG and dosage data. In an embodiment, each user may view customized information without turning to look at a display to select the information.

In an embodiment, the eyewear 210 is a portable eyewear viewer that displays key dynamic patient information such as hemodynamic data, cardiology waveforms, vital signs, etc. Eyewear 210 allows a user to view information without turning his or her head to view an LCD or CRT monitor. Although the eyewear headset 210 allows users to view data while working "heads down" on a patient, resolution may be limited for image review and/or fine text review, for example. When a user wishes to view detailed information or a finer degree of granularity, the user may look at a larger display device in the healthcare environment.

An eye or gaze tracking capability of the headset 210 and/or processor 230 may be used to control a display device, such as the display device 110. For example, the processor 230 detects when a user is looking at a certain button, option or feature on a display and selects or activates the button, option or feature for the user. Activation of an option/feature may also be based on an amount of time a user is looking/has looked at a certain area. The eyewear system 200 may also be used in conjunction with voice commands and/or gestures to control the display device 110 and/or other systems or features, for example.

In an embodiment, a user looks at the display device 110. The gaze tracking processor 230 recognizes that the user wants to see certain information and displays context-sensitive information for the patient on the display device 110, for example. Information on gaze and/or head position may be relayed from the processor 230 to determine information on the display device 110. Additionally, user preference information, information from the display device 110, and/or other input may be transmitted to configure the contents and/or other parameters of the display device 110.

In an embodiment, information displayed on the display device 110 may be determined based on rules and/or perspectives, for example. For example, rules determine that a doctor's gaze takes precedence over a nurse's gaze. Then, when the doctor turns away from the display device 110, the nurse gains control of the display device 110. Alternatively, control of the display device 110 may be shared by multiple users and common information displayed on display device 110 so that multiple users may be accommodated at approximately the same time.

The processor 230 and/or other processor or system related to the display device 110 may have an ability to arbitrate conflicts and priority among a plurality of users seeking access determine which user(s) should take control of the display device 110. For example, rules-based display control and/or hanging protocols may govern which user has control and priority and/or which users may share control and display area. Rules and other protocols may also govern when control over the display device 110 is relinquished and/or pre-empted.

In an embodiment, video switchboxes and/or voice commands may be used with image-guided surgery to switch displays so that only image-guided surgery information is viewed. In an embodiment, voice control and/or gestures may be used in conjunction with eye tracking to control the display device 110 and/or a system cursor.

In an embodiment, a user, such as a radiologist, may review images via the display device 110. The user may identify one or more of the images as significant images. In an embodiment, access to significant images may be streamlined or shortcut. For example, a user may access one or more significant images with a single click of a mouse button or other simple selection to reduce a user's effort in locating significant images when reviewing an exam or collection of images. A medical information system, such as a PACS system, may store significant image information to enable simplified retrieval of significant images by a user.

A visual tracking system, such as the tracking system 120 and/or the viewing system 200, may be integrated into an information system, such as a PACS workstation, and/or work in conjunction with an information system to track an amount of time a user, such as a radiologist, spends viewing each image in an exam or collection, for example. The visual tracking system may be used to track a location at the display device 110 at which the user is looking. Based on location and duration information, the information system, such as a PACS, may present images to the user, such as a radiologist, in a more efficient manner.

Certain embodiments allow a user to use a more natural way of creating hanging protocols for a radiology workstation, by making use of eye tracking and voice command and control. Eye tracking enables a system to track the eye movement of a user. The eye tracking can enable the workstation to move the mouse cursor by looking at specific locations of the screen. Voice command and control enables a user to command and control voice enabled applications. Combining these two technologies can create a new method for creating and managing Hanging Protocols with PACS client workstations.

Figure 3:
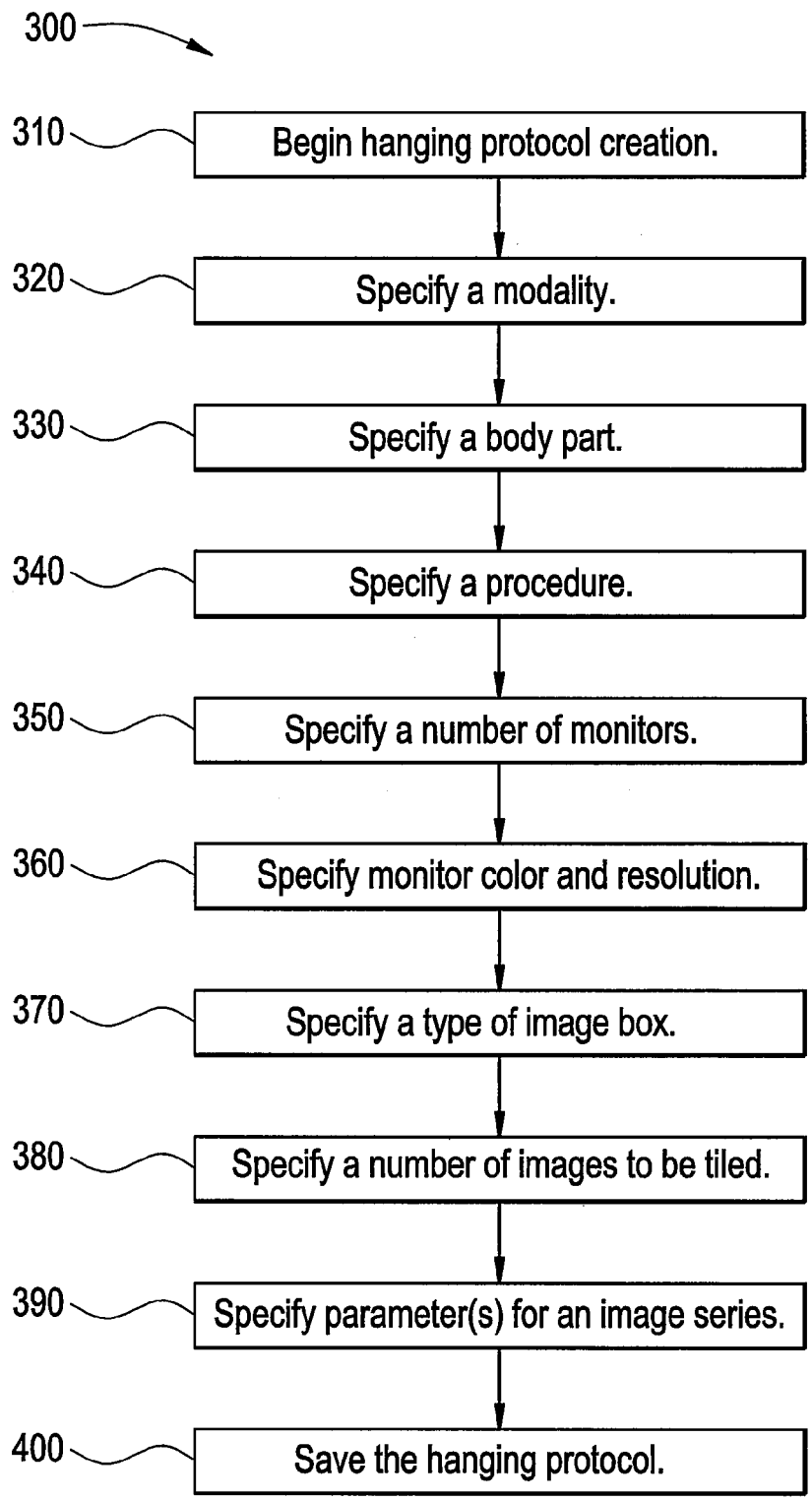
FIG. 3 illustrates a flow diagram for a method for creation of a hanging protocol using eye tracking and/or voice command and control in accordance with an embodiment of the present invention.

FIG. 3 illustrates a flow diagram for a method 300 for hanging protocol creation using eye tracking and/or voice command and control in accordance with an embodiment of the present invention. At step 310, hanging protocol creation begins. For example, voice command triggering of a hanging protocol creation command launches a hanging protocol creation tool of a PACS workstation. At step 320, a modality is specified. For example, a voice command of "Modality <modality code>" serves to specify the modality for hanging protocol creation. Modality code may include MR, CT, CR, etc.

At step 330, a body part is specified. For example, a voice command of "Body Part <body part name*>", such as "Body Part Head" can be used to specify one or more body parts with a hanging protocol. At step 340, a procedure is specified. For example, a voice command of "Procedure <procedure name*>" allows a user to specify one or more procedure names with the hanging protocol.

Figure 4:
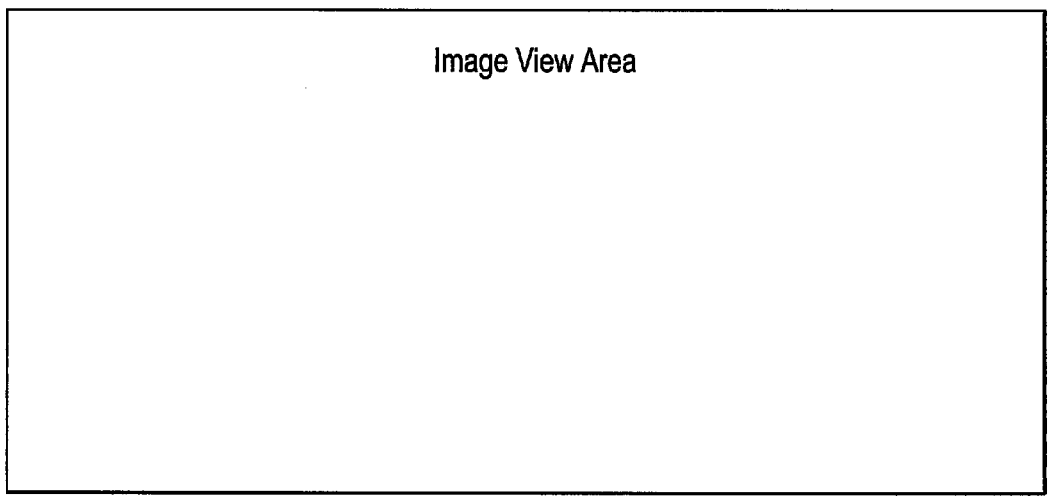
FIG. 4 illustrates an image view area for hanging protocol creation in accordance with an embodiment of the present invention.

At step 350, a number of monitors for use in the hanging protocol is specified. For example, a voice command such as "Num Monitor <number>" may be used to set a number of monitors for hanging protocol creation. For example, "Num Monitor 3" specifies a three-monitor PACS workstation. As another example, a user may look at an image view area, such as the image view area shown in FIG. 4, to specify the number of monitors.

Figure 5:
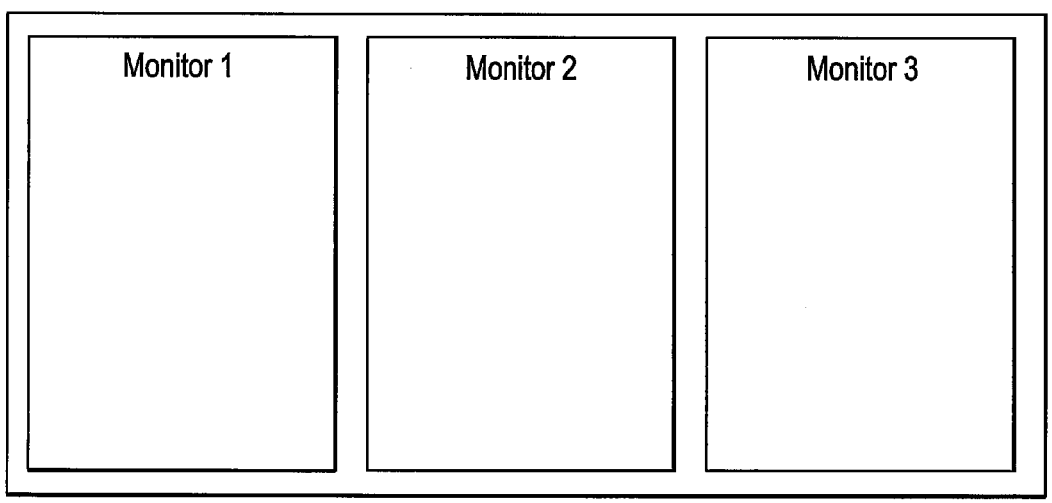
FIG. 5 illustrates an image view area for hanging protocol creation divided into three monitors in accordance with an embodiment of the present invention.

At step 360, a color and resolution is specified for the one or more monitors. For example, a voice command "Color" may be used to indicate a color monitor. A voice command "High Resolution" may indicate a high resolution monitor, for example. As another example, a user may look at each of the monitors in the image view area of the hanging protocol creation tool, such as the three monitors shown in FIG. 5, and say "Color" for a color monitor and "High Resolution" for a high resolution monitor.

Figure 6:
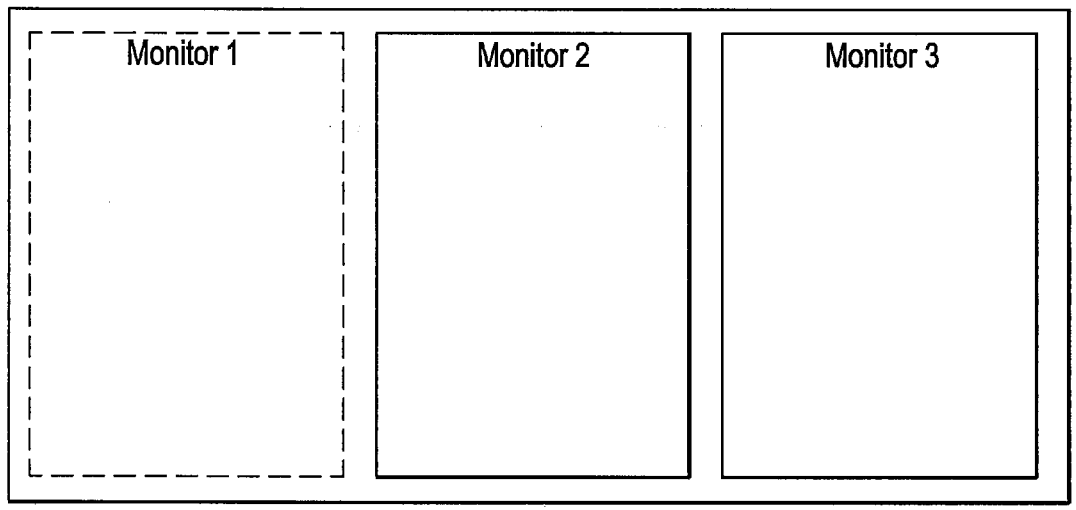
FIG. 6 illustrates a selection of a monitor in an image view area, such as by using eye tracking, in accordance with an embodiment of the present invention.
Figure 7:
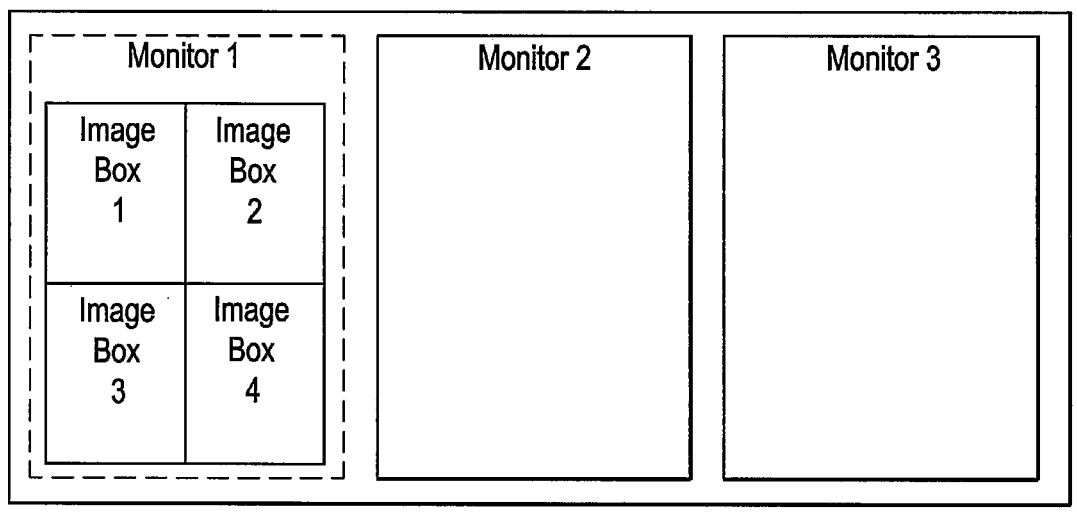
FIG. 7 illustrates dividing a monitor into multiple image boxes, such as by invoking voice command, in accordance with an embodiment of the present invention.

At step 370, a number of image boxes may be specified for each region. For example, a voice command "Num Image Boxes <number>" may be used to specify a number of images in a viewing region. As another example, a user may look at each monitor in the hanging protocol creation tool view area and say "Num Image Boxes <number>." For example, to specify four image boxes for the first monitor, a user looks at the first monitor (see, e.g., FIG. 6) and says "Image Boxes 4." FIG. 7 illustrates a monitor divided into four image boxes per eye tracking and voice command.

Figure 8:
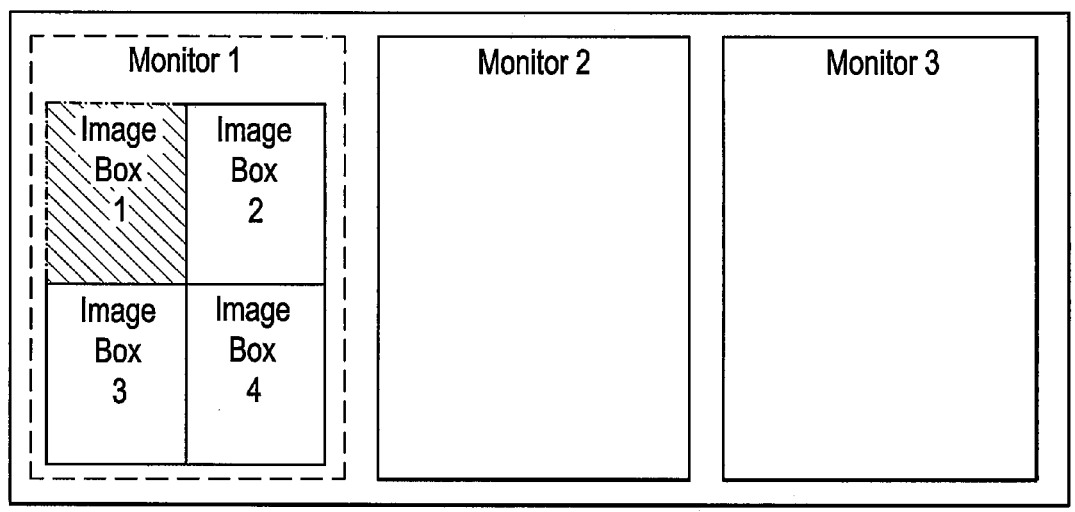
FIG. 8 illustrates selecting an image box for specifying an image box description, such as by using eye tracking, in accordance with an embodiment of the present invention.

At step 380, a type of image box is specified. For example, a voice command "Image Box Type <type>" may be used to specify image box type such as stack, sheet, volume, etc. As another example, a user may look at each of the image boxes in the hanging protocol creation tool and say "Image Box Type Stack" to specify, for example, that an image box is a stack. For example, FIG. 8 illustrates looking at image box 1 in monitor 1 to specify an image box type.

At step 390, a number of images to be tiled in an image box is specified. For example, a voice command "Image Box Upcount <number>" may be used to allow the hanging protocol creation tool to specify a number of images tiled in an image box. As another example, a user may look at each of the image boxes in the hanging protocol creation tool and say "Image Box Upcount <number>." For example, to specify an upcount to be four on a sheet image box, a user looks at a monitor area and says "Image Box Upcount 4."

At step 400, one or more parameters may be specified for an image series to be loaded in one or more image boxes. For example, a voice command such as "Parameter <parameter name, value>" may be used to specify an image box parameter. As another example, a user may look at each of the image boxes (see, e.g., FIG. 8) in the hanging protocol and issue the command "Parameter <parameter name, value>" to set parameters for selecting a proper set of images.

At step 410, the hanging protocol is saved. For example, a voice command such as "Save <hanging protocol name>" and/or eye tracking movement may be used to save the hanging protocol.

The steps described above use eye tracking mechanism for moving/selecting the cursor and voice command to control the behavior of the hanging protocol.

For example, a hanging protocol specification may include an image box type (e.g., stack, sheet, volume, etc.). A specification may include an upcount (e.g., 1, 2, 4, 6, 8, etc.). A specification may include a modality (e.g., magnetic resonance, computed tomography, X-ray, ultrasound, etc.). Additionally, a specification may include a body part (e.g., head, neck, chest, limb, etc.). A specification may further include a list of one or more procedures involved. A specification may also include a comparison indication (e.g., yes or no). In certain embodiments, a specification includes one or more series selection parameters (for example, one or more parameter names and values, such as parameter=slice thickness, value=3 mm, etc.). A specification may include other configuration information and/or settings, for example.

Thus, certain embodiments provide a more natural way for a user to create hanging protocols for an image viewing (e.g., radiology) workstation. Certain embodiments allow eye tracking and/or voice command and control to be used to create hanging protocols. In certain embodiments, an eye tracking mechanism may be used to control a viewing station cursor, and a voice command may be used to control behavior of the hanging protocol. Certain embodiments provide a technical effect of touch free creation and/or management of hanging protocols via a workstation, such as a PACS client workstation, using eye tracking and voice command/control.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A computer-implemented method for creating a hanging protocol based on at least one of eye tracking and voice command and control input in a clinical environment, said method comprising:
    specifying creation of a hanging protocol specification to format, organize, and present clinical images on a display using user input including a combination of eye tracking and voice command and control to configure and control behavior of the hanging protocol, said specifying comprising:
        specifying one or more of a modality, a body part, and a procedure for said hanging protocol using said user input;
        specifying at least one monitor characteristic for use in said hanging protocol using said user input, said at least one monitor characteristic comprising at least one of a number of monitors, a monitor color and a monitor resolution; and
        specifying at least one image box characteristic for one or more regions in a monitor using said hanging protocol using said user input, said at least one image box characteristic comprising a number of image boxes for a monitor region, a type of image box, a number of tiled images in an image box, and at least one image box parameter;
    translating, using a processor, said input into a hanging protocol; and
    facilitating, using a processor, display of clinical information based on said hanging protocol.

2. The method of claim 1, further comprising saving said hanging protocol.

3. The method of claim 1, further comprising using eye tracking to move a cursor in said hanging protocol and using voice command to control behavior of said hanging protocol.

4. A computer-implemented method for hanging protocol creation and management using eye tracking and voice command and control input in a clinical environment, said method comprising:
    initiating, using a processor, hanging protocol creation, the hanging protocol creation using a combination of eye tracking and voice command input;
    accepting user input to create a hanging protocol to format, organize, and present clinical images on a display using input including a combination of eye tracking and voice command and control to configure and control behavior of the hanging protocol, said creation comprising:
    specifying a body part for said hanging protocol using at least one of eye tracking and voice command input;
    specifying a clinical procedure for said hanging protocol using at least one of eye tracking and voice command input;
    identifying a number of monitors for use in said hanging protocol using at least one of eye tracking and voice command input;
    defining at least one of a monitor color and monitor resolution for one or more monitors in said hanging protocol using at least one of eye tracking and voice command input;
    specifying a number and type of image box for a viewing region in said one or more monitors in said hanging protocol using at least one of eye tracking and voice command input;
    specifying a number of images to be tiled in an image box in said hanging protocol using at least one of eye tracking and voice command input;

translating, using a processor, said input into a hanging protocol; and saving said hanging protocol to facilitate, using a processor, display of clinical information based on said hanging protocol.

5. The method of claim 4, further comprising defining one or more parameters for an image series to be loaded in one or more image boxes in said hanging protocol using at least one of eye tracking and voice command input.

6. The method of claim 4, further comprising displaying clinical image data using said hanging protocol.

7. A tangible computer-readable storage medium having a set of instructions for execution on a computer, said set of instructions comprising:

an input routine receiving user input to configure a hanging protocol for clinical information viewing, said user input including 1) eye tracking and 2) voice command and control to configure and control behavior of the hanging protocol to format, organize, and present clinical information on a display; and a hanging protocol configuration routine translating said user input into a hanging protocol for facilitating display of clinical information, wherein said hanging protocol configuration routine configures one or more of a modality, a body part, and a procedure for said hanging protocol based on said user input, wherein said hanging protocol configuration routine configures at least one monitor characteristic for use in said hanging protocol based on said user input, said at least one monitor characteristic comprising at least one of a number of monitors, a monitor color and a monitor resolution, wherein said hanging protocol configuration routine configures at least one image box characteristic for one or more regions in a monitor in said hanging protocol based on user input, said at least one image box characteristic comprising a number of image boxes for a monitor region, a type of image box, a number of tiled images in an image box, and at least one image box parameter.

8. The computer-readable medium of claim 7, wherein said hanging protocol configuration routine saves said hanging protocol for later use.

9. The computer-readable medium of claim 7, wherein said input routine receives user input include eye tracking information used to move a cursor in said hanging protocol and voice command information used to control behavior of said hanging protocol.

* * * * *